United States Patent
Entabi (10) Patent No.: US 11,224,494 B2
(45) Date of Patent: Jan. 18, 2022

(54) ERGONOMICALLY BALANCED SURGICAL INSTRUMENTS HOLDER

(71) Applicant: Fateh Entabi, Visalia, CA (US)

(72) Inventor: Fateh Entabi, Visalia, CA (US)

( * ) Notice: Subject to any disclaimer, the term of this patent is extended or adjusted under 35 U.S.C. 154(b) by 169 days.

(21) Appl. No.: 15/869,669

(22) Filed: Jan. 12, 2018

(65) Prior Publication Data

US 2019/0216566 A1    Jul. 18, 2019

(51) Int. Cl.
*A61B 50/22* (2016.01)
*F16M 13/04* (2006.01)
*A61B 50/00* (2016.01)

(52) U.S. Cl.
CPC .............. *A61B 50/22* (2016.02); *F16M 13/04* (2013.01); *A61B 2050/002* (2016.02)

(58) Field of Classification Search
CPC ... A61B 50/22; A61B 50/24; A61B 2050/002; F16M 13/04
USPC ....................................................... 211/85.13
See application file for complete search history.

(56) References Cited

U.S. PATENT DOCUMENTS

| | | | | |
|---|---|---|---|---|
| 3,476,257 A | * | 11/1969 | O'Connell | B60R 7/08 211/13.1 |
| D243,559 S | * | 3/1977 | Hoyle | D28/38 |
| 4,748,125 A | * | 5/1988 | Pizzolante | B01L 9/06 206/460 |
| D305,944 S | * | 2/1990 | Mellott | D11/146 |
| 5,046,624 A | * | 9/1991 | Murphy | A47F 7/0028 206/370 |
| 5,380,493 A | * | 1/1995 | Chavez | B01L 9/50 211/85.13 |
| 5,975,295 A | * | 11/1999 | Diamond | A61M 5/008 206/366 |
| 6,209,732 B1 | * | 4/2001 | Dennis | A45D 1/04 211/70.6 |
| 6,279,743 B1 | * | 8/2001 | Ballard | A61M 5/3213 128/852 |
| D469,926 S | * | 2/2003 | Petruccelli | D28/73 |
| D487,170 S | * | 2/2004 | Petruccelli | D28/73 |
| D728,819 S | * | 5/2015 | Schaffer | D24/232 |
| D791,340 S | * | 7/2017 | Schaffer | D24/232 |
| 2002/0014560 A1 | * | 2/2002 | Diamond | A61M 5/008 248/37.3 |
| 2003/0024891 A1 | * | 2/2003 | Diamond | A61M 5/008 211/85.13 |

(Continued)

*Primary Examiner* — Stanton L Krycinski (57) ABSTRACT

It is the first surgical instrument holder designed specifically to maximize the efficiency of instrument exchange during surgery. It sits on top of the patient laying on the operating room table and fits the curvature of the average human torso while it places the chambers that hold the surgical instruments at the most natural angle for the hand of the standing surgeon. The size of the chambers is designed so it fits most laparoscopic surgical instruments in use today. It has two openings, an entrance opening and an exit opening. The entrance opening faces the surgeon and designed to enable the surgeon to insert the instrument without having to look at the holder. That enables the surgeon eyes to remain completely focused on the surgical field. That may increase the efficiency of instrument exchange. Which increases the efficiency of the operation. It also prevents the instruments from falling on the floor and the potential to break.

10 Claims, 7 Drawing Sheets

(56) References Cited

U.S. PATENT DOCUMENTS

| | | | | |
|---|---|---|---|---|
| 2004/0206711 | A1* | 10/2004 | Hoftman | A61B 50/22 211/85.13 |
| 2013/0001180 | A1* | 1/2013 | Stout | A61B 50/22 211/85.13 |
| 2013/0277322 | A1* | 10/2013 | Tiberio | A61B 50/20 211/74 |
| 2016/0000993 | A1* | 1/2016 | Endyk | A61M 5/008 211/85.13 |

* cited by examiner

ERGONOMICALLY BALANCED SURGICAL INSTRUMENTS HOLDER

BACKGROUND OF THE INVENTION

Field of the Invention

The present invention relates to a device to organize, stabilize and prevent surgical instruments from falling to the ground.

Background Art

In the majority of laparoscopic operations the surgeon stands on the left side of the patient. To the surgeon's right side, there lies the head of the patient and the anesthesiologist. That leaves no room for an assistant or an instrument stand. Currently, most surgeons place their surgical instruments on the patient's chest. These instruments are at risk of falling on the floor without any reliable mechanism to prevent that. These surgical instruments are very expensive and fragile, thus they frequently break when they fall. There are some inventions that provide some help. However, none of them are good enough. One example is a soft plastic bag that adheres to the drapes. Since it is soft, the opening of the bag collapses on itself when empty. That makes it difficult to insert the instruments inside it. In addition the bag breaks frequently when the instrument is inserted in a trajectory different from the bag alignment. Another prior art is a rigid holster that lies vertically and dangles off the side of the drape. The holster puts undue tension on the drape that causes it to slip. In addition, since it stands vertically, it is very awkward for the surgeon to aim the instrument in the holster.

BRIEF SUMMARY OF THE INVENTION

This is a surgical instrument holder designed to be used during an operation. It is specifically designed to put the instrument at the optimal ergonomic angle in relationship to the standing surgeon's hand. It is versatile, as it adheres to the surgical drape or the bare skin of the patient. Since it has a rigid large opening, it enables the surgeon to insert the instrument inside the holder with minimal effort and possibly without even looking. That may improve operative time, decrease surgeon's distractions, and decrease the risk of instruments falling on the floor. This invention is most beneficial when multiple surgical instruments are being used sequentially and alternatively, as it allows for a quick exchange between instruments to aim the instrument in the holster.

DETAILED DESCRIPTION OF THE INVENTION

Figure 1:
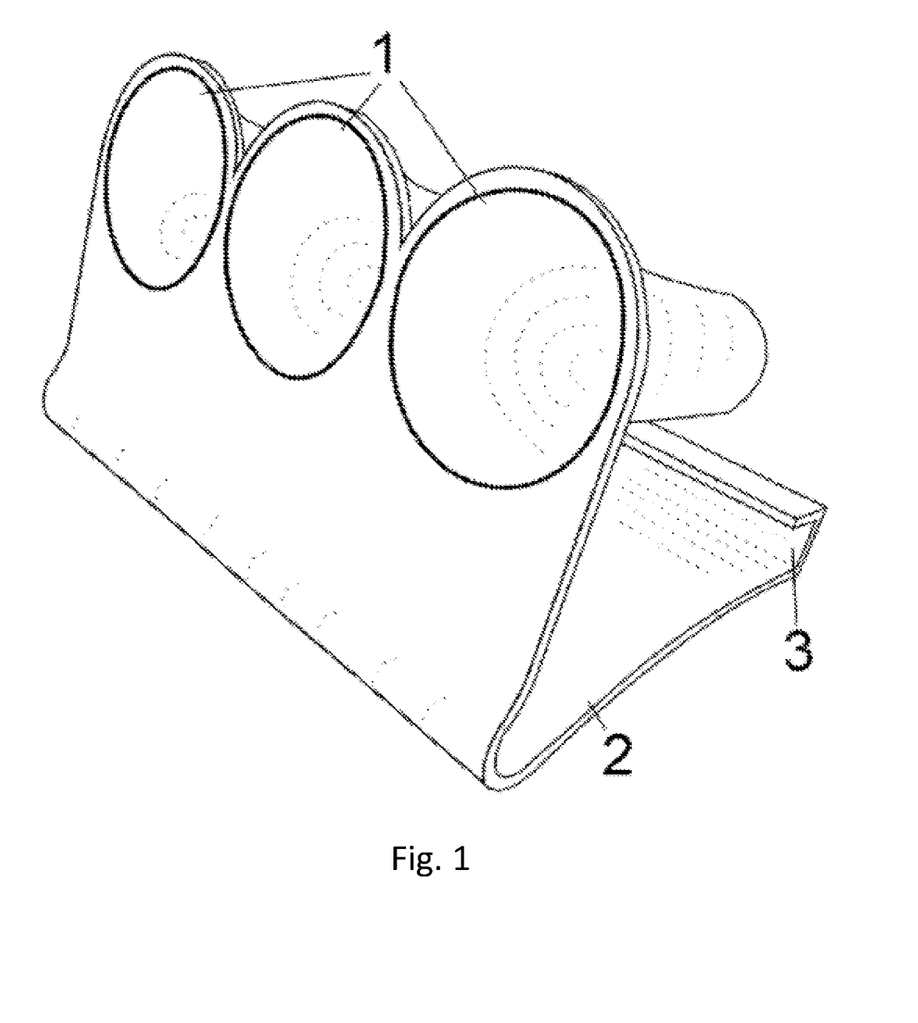
FIG. 1 is an axonometric perspective view of the invention with a double sided tape as an embodiment of the adhesion mechanism.
Figure 2:
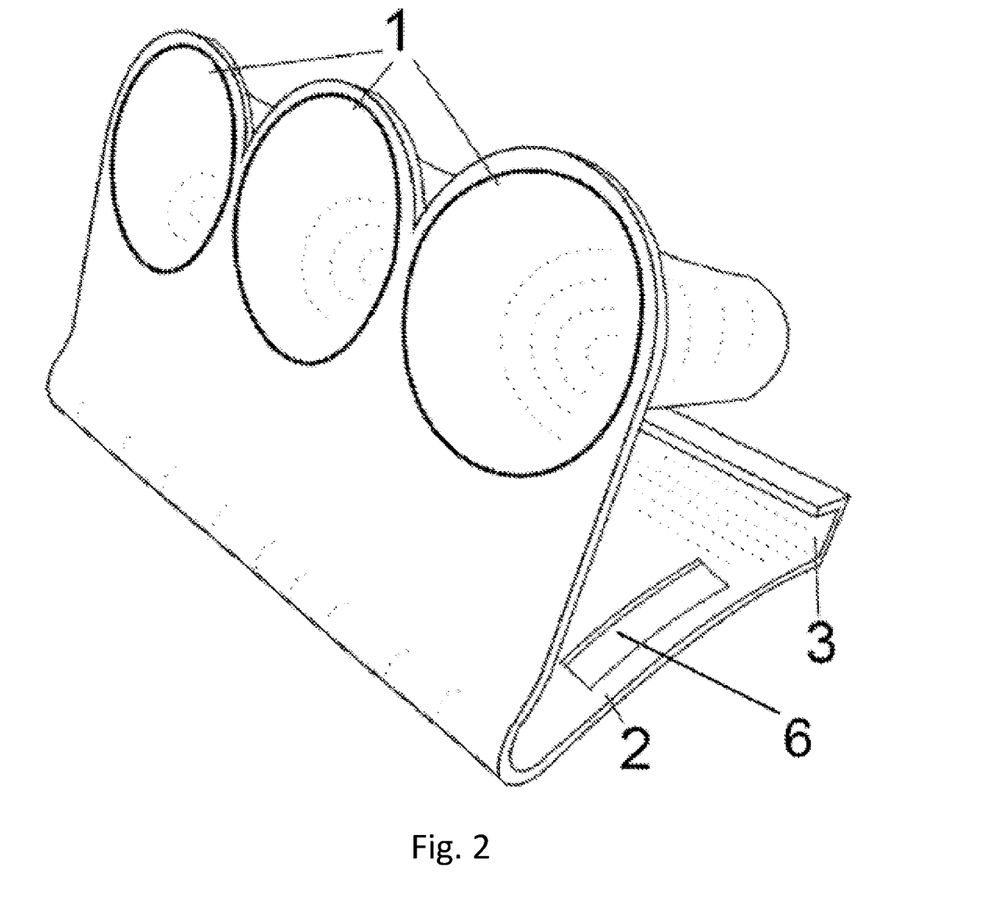
FIG. 2 is an axonometric perspective view of the invention with an opening or indentation for an external clamping mechanism as an embodiment of the adhesion mechanism.
Figure 3:
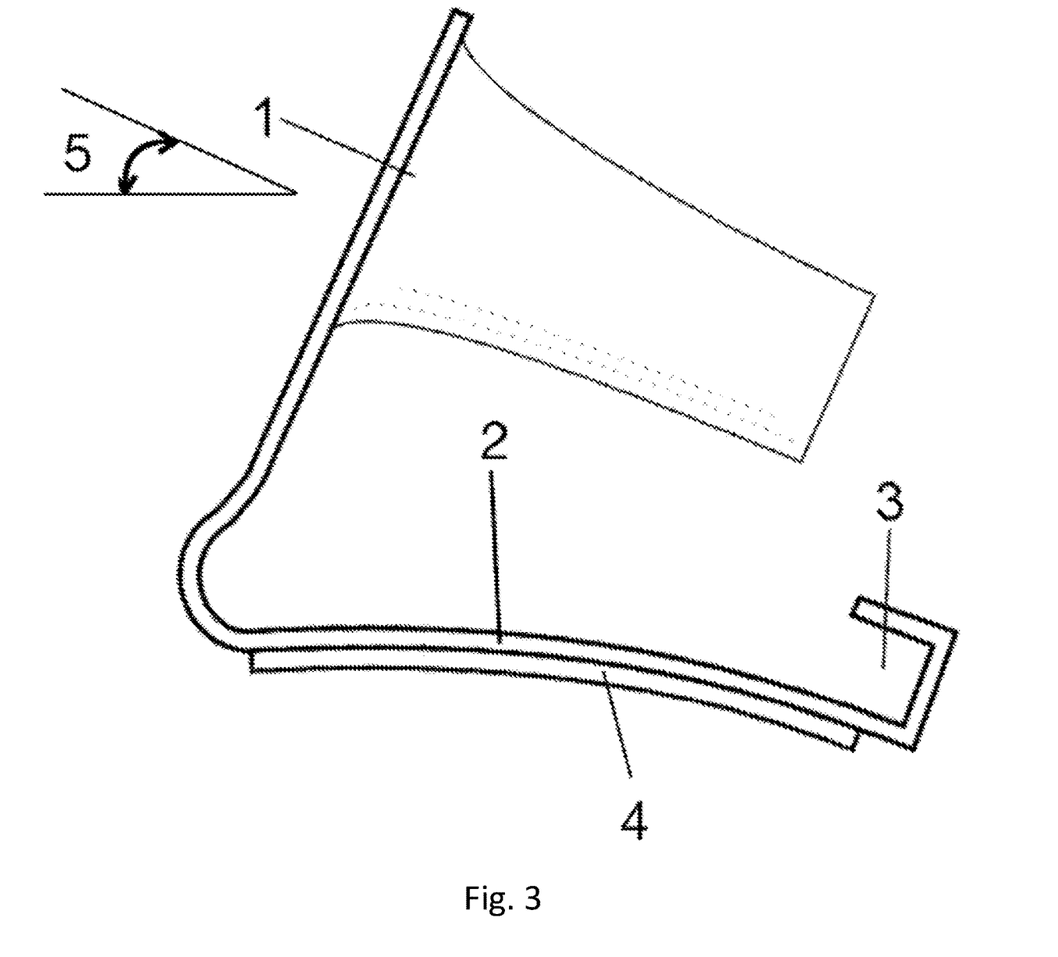
FIG. 3 is a side orthotopic view of the invention with a double sided tape as an embodiment of the adhesion mechanism.
Figure 4:
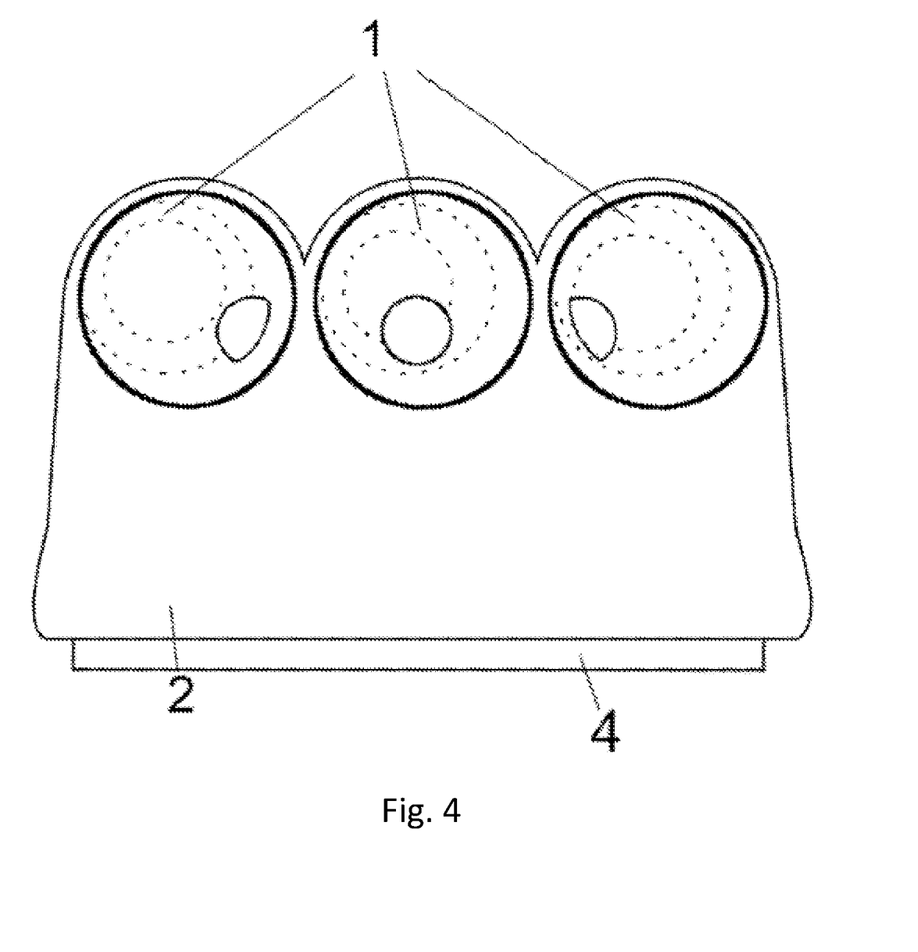
FIG. 4 is a front perspective view of the invention with a double side tape as an embodiment of the adhesion mechanism.
Figure 5:
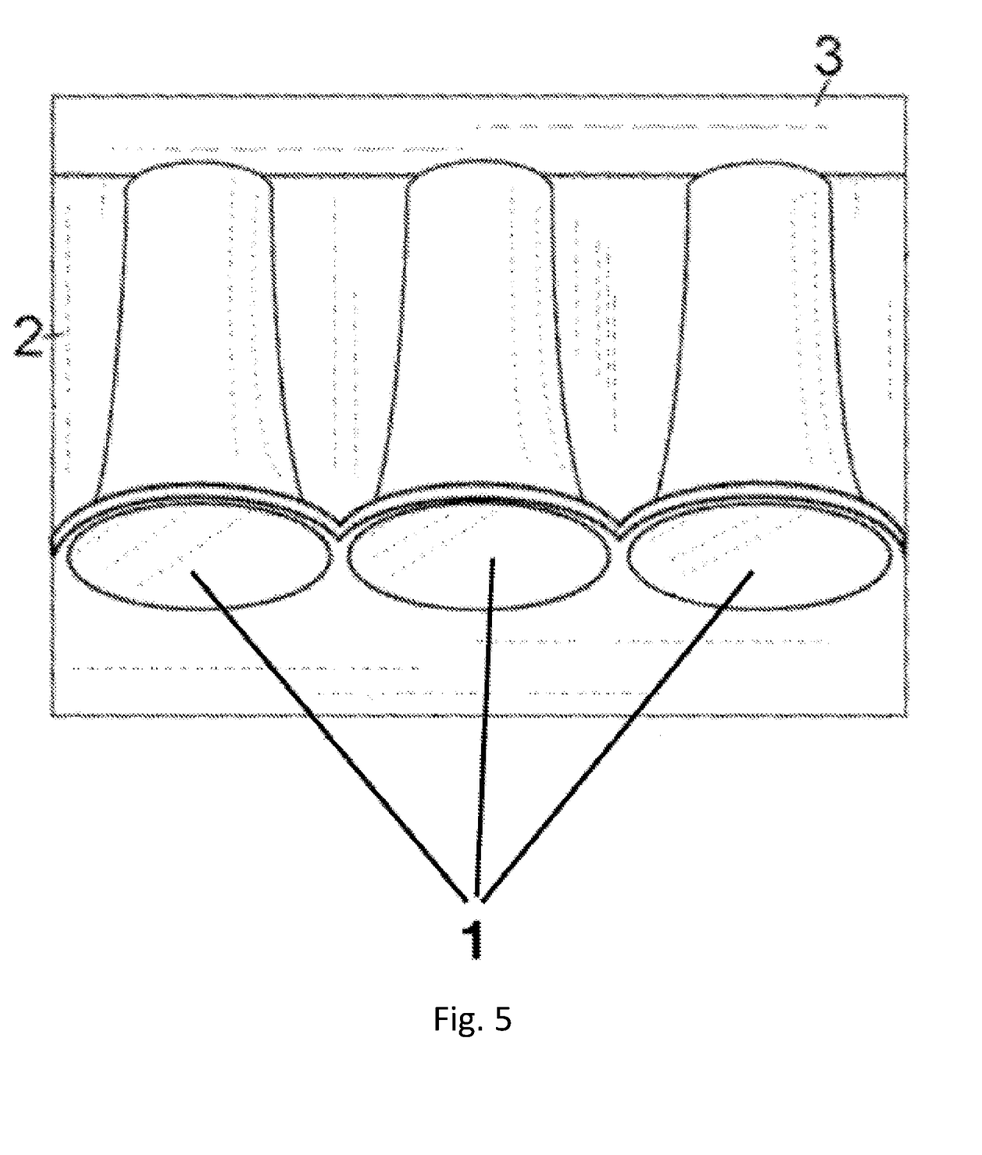
FIG. 5 is a top orthotopic view of the invention with a double sided tape as an embodiment of the adhesion mechanism.
Figure 6:
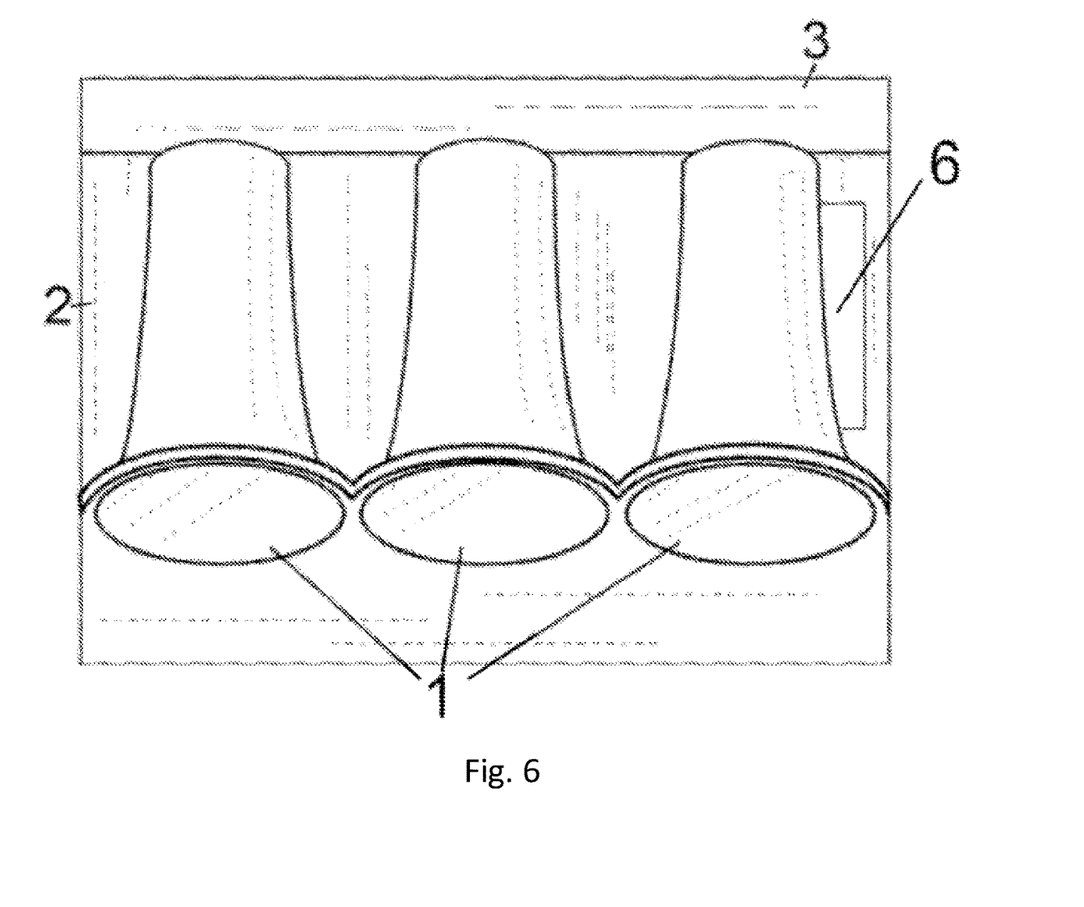
FIG. 6 is a top orthotopic view of the invention with an opening or indentation for an external clamping mechanism as an embodiment of the adhesion mechanism.
Figure 7:
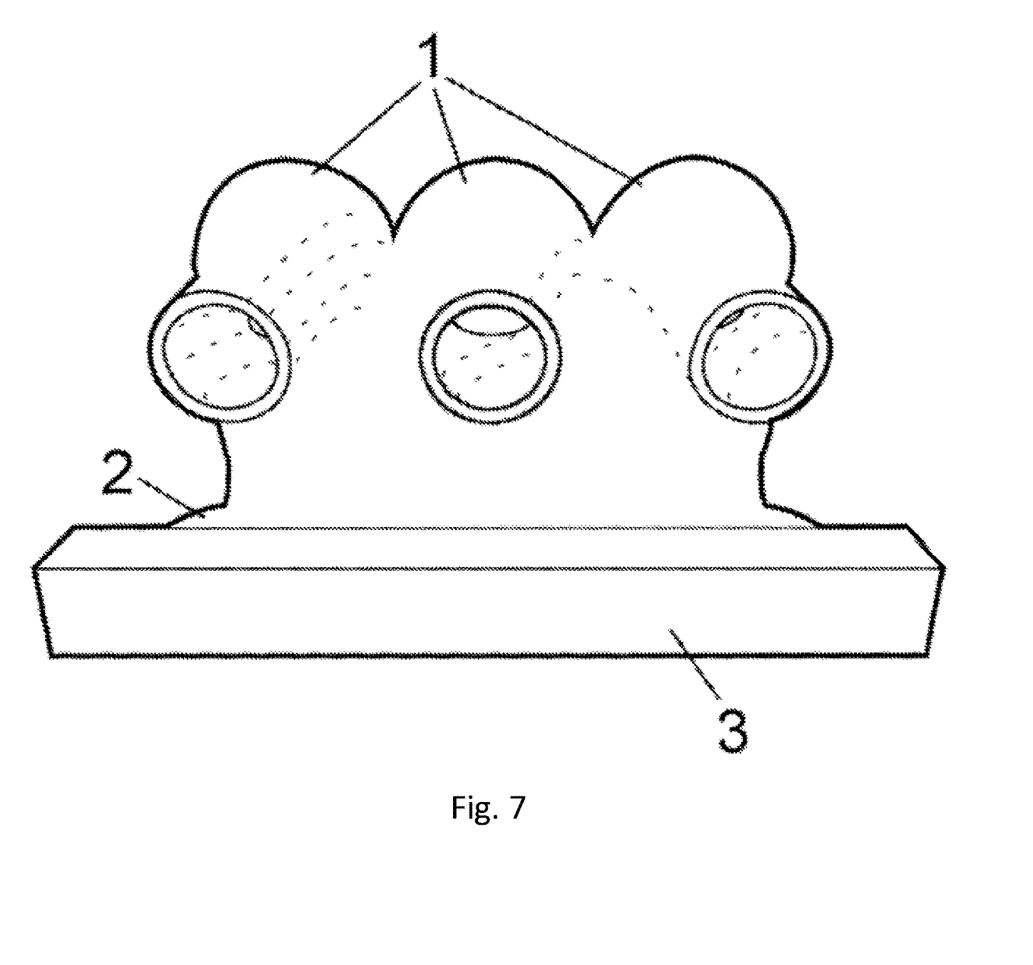
FIG. 7 is a back perspective view of the invention with an opening or indentation for an external clamping mechanism as an embodiment of the adhesion mechanism.

The surgical instrument holder includes a body with chambers 1 aligned on a plane. The surgical instrument holder also includes a base 2 attached to the body, and a channel 3 along an edge of the base 2. The chambers 1 are cone shaped or funnel shaped chambers with a wide entrance opening at the side facing the surgeon and a narrower exit opening on the other side that fits most of the laparoscopic surgical instruments in use today. The entrance opening and exit opening can be circular with a diameter of the entrance opening being twice the diameter of the exit opening. It is designed so the surgical instruments can enter from the entrance opening, and protrude on the other side from the exit opening. The entrance opening is large enough to allow most instruments to go through it. However, it is not large enough to allow for the instrument's handle to go through. Thus, the entrance opening holds the instruments in their location and prevents them from going completely through the chamber 1 and through the instrument holder. The chambers 1 are aligned at an angle 5 with the horizontal plane that makes it optimal for the standing surgeon's dominant hand. The angle 5 is between 0 and 89 degrees, and more specifically 24 degrees. The channel 3 can accommodate a tubular structure, and can stabilize a tubing or a wire used in surgery. The surgical instrument holder is made from a single piece of injection molded hard plastic, such that the body and the base 2 are made from one solid piece. The body and the base 2 can also be made of metal, and the body and the base 2 can be made from two different pieces. The base 2 includes a double-sided tape 4 on its bottom to help it adhere to the surface underneath. The base can also include an indentation or opening 6 that can accommodate an external clamping mechanism, such as a clip. The surgical instrument holder can be packaged and sterilized. It is the first ergonomically configured surgical instrument holder that enables efficient instrument exchange during an operation.

The invention claimed is:

1. A surgical instrument holder, comprising:
   a body comprised of multiple chambers, each chamber is funnel shaped having one entrance opening and one exit opening, said entrance opening being larger than said exit opening, said entrance opening configured to hold an instrument and prevent the instrument from going completely through the chamber, said chambers are aligned on a plane, said plane is at an angle with the horizontal plane, said angle is between 0 and 89 degrees;
   a base attached to said body, said base has a curvature such that said base is curved from a proximal edge attached to an edge of said body to a distal edge, said curvature configured to allow said base to fit a curvature of a torso;
   said base further comprising a channel along said distal edge, said channel having an open side extending in a longitudinal direction of the channel and the distal edge, said channel configured to accommodate a tubular structure and to stabilize a tubing or a wire used in surgery; and an adhesion mechanism attached to said base, said adhesion mechanism is made of a double sided tape, said adhesion mechanism configured to allow said base to adhere to skin or a drape.

2. A surgical instrument holder according to claim 1 in which said angle is 24 degrees.

3. A surgical instrument holder according to claim 1 in which there are three of said chambers.

4. A surgical instrument holder according to claim 1 in which said body and said base are made from one solid piece.

5. A surgical instrument holder according to claim 1 in which said body and said base are made from two different pieces.

6. A surgical instrument holder according to claim 1 in which said body and said base are made of plastic.

7. A surgical instrument holder according to claim 1 in which said body and said base are made of metal.

8. A surgical instrument holder according to claim 1 in which said adhesion mechanism is further comprised of an indentation or an opening configured to accommodate an external clamping mechanism.

9. A surgical instrument holder according to claim 1 in which said chambers are configured to retain a variety of laparoscopic instruments.

10. A surgical instrument holder according to claim 1 in which the entrance opening and the exit opening are circular, and said entrance opening has a diameter twice a diameter of said exit opening.

* * * * *